(12) United States Patent
Kleinhaus (10) Patent No.: US 11,318,290 B2
(45) Date of Patent: May 3, 2022

(54) RIBBED DILATOR TIP

(71) Applicant: BOSTON SCIENTIFIC SCIMED, INC., Maple Grove, MN (US)

(72) Inventor: Matthew Kleinhaus, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 84 days.

(21) Appl. No.: 16/570,071

(22) Filed: Sep. 13, 2019

(65) Prior Publication Data

US 2020/0086095 A1    Mar. 19, 2020

Related U.S. Application Data

(60) Provisional application No. 62/732,879, filed on Sep. 18, 2018.

(51) Int. Cl.
*A61M 29/00* (2006.01)
*A61B 17/00* (2006.01)

(52) U.S. Cl.
CPC ..... *A61M 29/00* (2013.01); *A61B 2017/0084* (2013.01); *A61B 2017/00305* (2013.01)

(58) Field of Classification Search
CPC ........ A61B 2017/3454; A61B 17/3417; A61B 2017/346; A61M 2025/0687; A61M 25/0067–0069; A61M 2025/0073
See application file for complete search history.

(56) References Cited

U.S. PATENT DOCUMENTS

| | | | | |
|---|---|---|---|---|
| 4,596,548 | A  * | 6/1986 | DeVries | A61M 25/0069 604/264 |
| 8,034,074 | B2 | 10/2011 | Garner et al. | |
| 8,491,620 | B2 | 7/2013 | Brasington et al. | |
| 2005/0149096 | A1* | 7/2005 | Hilal | A61M 25/0069 606/191 |
| 2005/0149097 | A1 | 7/2005 | Regnell et al. | |
| 2005/0171591 | A1* | 8/2005 | McHale | A61M 25/0068 623/1.11 |
| 2006/0129181 | A1 | 6/2006 | Callol et al. | |
| 2006/0253102 | A1* | 11/2006 | Nance | A61M 25/0023 604/525 |
| 2007/0244440 | A1* | 10/2007 | Pal | A61M 25/0074 604/164.13 |

(Continued)

FOREIGN PATENT DOCUMENTS

WO    2008106085 A1    9/2008

OTHER PUBLICATIONS

Ballard et al; "In Vitro Evaluation of the Insertion Force for Different Dilator Tip Configurations," Journal of Vascular and Interventional Radiology, 24, 1906-1909, 2013.

(Continued)

*Primary Examiner* — Thomas Mcevoy
(74) *Attorney, Agent, or Firm* — Seager, Tufte & Wickhem, LLP (57) ABSTRACT

A dilator tip may include an elongated tubular member defined by a circumferential wall and having a distal tip region and a proximal end, and a plurality of ribs extending longitudinally between the distal tip region and the proximal end. The plurality of ribs may extend radially outward from the elongated tubular member, and the plurality of ribs may be spaced apart circumferentially.

20 Claims, 10 Drawing Sheets

(56) References Cited

U.S. PATENT DOCUMENTS

| | | | |
|---|---|---|---|
| 2007/0255305 A1 | 11/2007 | McMichael et al. | |
| 2010/0324488 A1* | 12/2010 | Smith ................ | A61B 17/3417 |
| | | | 604/164.11 |
| 2012/0130417 A1 | 5/2012 | Lepulu et al. | |
| 2014/0296706 A1 | 10/2014 | Chronos et al. | |
| 2015/0057680 A1 | 2/2015 | Chotenovsky et al. | |

OTHER PUBLICATIONS

International Search Report and Written Opinion dated Nov. 27, 2019 for International Application No. PCT/US2019/051003.

* cited by examiner

RIBBED DILATOR TIP

CROSS-REFERENCE TO RELATED APPLICATIONS

This application claims the benefit of priority under 35 U.S.C. § 119 to U.S. Provisional Application Ser. No. 62/732,879, filed Sep. 18, 2018, the entirety of which is incorporated herein by reference.

TECHNICAL FIELD

The disclosure pertains to medical devices and more particularly to dilator tips for use with a sheath.

BACKGROUND

A wide variety of medical devices have been developed for medical use including, for example, medical devices that are passed through tissue walls and into the body. These medical devices may be used in a variety of regions of the body, and the physician may need to access the region of the body through one or more tissue walls. Of the known medical devices and methods, each has certain advantages and disadvantages. There is an ongoing need to provide alternative medical devices as well as alternative methods for manufacturing and using the medical devices.

SUMMARY

This disclosure provides design, material, manufacturing method, and use alternatives for medical devices. An example dilator tip comprises an elongated tubular member defined by a circumferential wall and having a distal tip region and a proximal end, and a plurality of ribs extending longitudinally between the distal tip region and the proximal end, the plurality of ribs extending radially outward from the elongated tubular member, the plurality of ribs spaced apart circumferentially.

Alternatively or additionally to the embodiment above, the elongated tubular member and plurality of ribs are all formed from a single monolithic piece.

Alternatively or additionally to the embodiment above, the elongated tubular member and the plurality of ribs are formed from a polymer.

Alternatively or additionally to the embodiment above, the plurality of ribs have a first height at the distal tip region and a second height at the proximal end, wherein the second height is larger than the first height.

Alternatively or additionally to the embodiment above, a radially outward facing top surface of each of the plurality of ribs extends from the distal tip region toward the proximal end at an angle of between 1 degree and 20 degrees.

Alternatively or additionally to the embodiment above, the dilator tip further comprises a proximal plate extending radially outward from the proximal end of the elongated tubular member, wherein the plurality of ribs extend between the distal tip region and the proximal plate.

Alternatively or additionally to the embodiment above, each of the plurality of ribs has a first width at a base adjacent the elongated tubular member, and a second width at a top surface of the rib, wherein the second width is larger than the first width.

Alternatively or additionally to the embodiment above, the plurality of ribs each has a flat top surface.

Alternatively or additionally to the embodiment above, the plurality of ribs includes 4-50 ribs.

Alternatively or additionally to the embodiment above, the plurality of ribs includes 20 ribs.

Alternatively or additionally to the embodiment above, the dilator tip further comprises a sheath attached to a proximal end of the plurality of ribs.

Alternatively or additionally to the embodiment above, a distal end of the sheath includes a plurality of pleats configured to conform to the ribs and spaces between the ribs.

Alternatively or additionally to the embodiment above, the plurality of pleats includes alternating peaks and valleys, wherein the peaks are configured to engage the ribs and the valleys are configured to be disposed within the spaces between the ribs.

Alternatively or additionally to the embodiment above, the valleys are configured to extend only partially into the spaces between the ribs.

Alternatively or additionally to the embodiment above, the sheath is disposed over only a proximal region of the ribs.

Another example dilator tip comprises an elongated tubular member defined by a circumferential wall and having a distal tip region, and a plurality of ribs extending longitudinally and proximally from the distal tip region, the plurality of ribs extending radially outward from the elongated tubular member, the plurality of ribs spaced apart circumferentially, wherein the plurality of ribs have a first height at the distal tip region and a second height at a proximal end thereof, wherein the second height is larger than the first height.

Alternatively or additionally to the embodiment above, each of the plurality of ribs has a first width at a base adjacent the elongated tubular member, and a second width at a top surface of the rib, wherein the second width is larger than the first width.

Alternatively or additionally to the embodiment above, the plurality of ribs includes 4-50 ribs.

Alternatively or additionally to the embodiment above, each of the plurality of ribs has a variable stiffness, with a distal portion of each rib adjacent the distal tip region having a first stiffness and a proximal portion of each rib adjacent the proximal end having a second stiffness, wherein the second stiffness is greater than the first stiffness.

Another example dilator tip comprises an elongated tubular member defined by a circumferential wall and having a distal tip region, a plurality of ribs extending longitudinally and proximally from the distal tip region, the plurality of ribs extending radially outward from the elongated tubular member, the plurality of ribs spaced apart circumferentially, wherein the plurality of ribs have a first height at the distal tip region and a second height at a proximal end thereof, wherein the second height is larger than the first height, and a sheath attached to a proximal end of the plurality of ribs, the sheath including a plurality of pleats configured to conform to the ribs and spaces between the ribs, the plurality of pleats including alternating peaks and valleys, wherein the peaks are configured to engage the ribs and the valleys are configured to be disposed within the spaces between the ribs.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "withdraw", variants thereof, and the like, may be generally considered with respect to the positioning, direction, and/or operation of various elements relative to a user/operator/manipulator of the device, wherein "proximal" and "withdraw" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following description should be read with reference to the drawings, which are not necessarily to scale, wherein similar elements in different drawings are numbered the same. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

Figure 1:
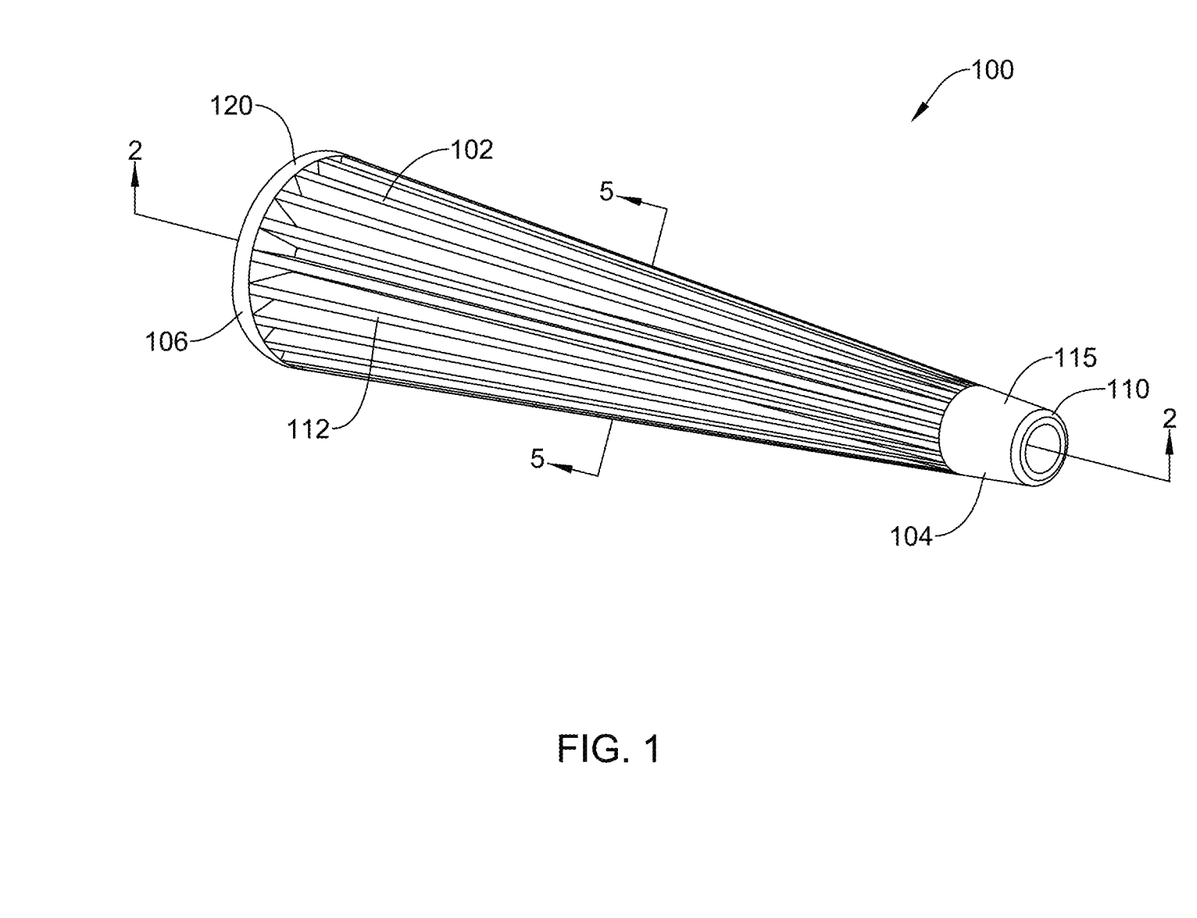
FIG. 1 is a perspective view of an example dilator tip.

As will be described in greater detail below, FIG. 1 illustrates an example dilator tip 100 which may be utilized with a dilator sheath. Specifically, FIG. 1 illustrates the dilator tip 100 having a distal end 110, a proximal end 120 and a plurality of circumferentially spaced apart ribs 102. The ribs 102 may extend longitudinally and proximally from a distal tip region 104. In some embodiments, the distal tip region 104 may be defined by a circumferential wall 115. The distal tip region 104 may be a truncated cone and the circumferential wall 115 may be a solid wall that is devoid of any slits, holes or openings extending through the wall. The outer surface of the dilator tip 100 may be defined by an outer circumferential surface of the distal tip region 104 and a radially outward facing top surface 112 of each rib 102. The plurality of spaced apart ribs 102 may reduce the overall surface area of the dilator tip 100 that engages tissue. This reduced surface area may provide the advantage of reducing the friction force of the dilator tip 100 as the dilator tip 100 is moved through tissue. For example, the top surface 112 of the plurality of ribs 102 may provide a 30% to 75% reduction in surface area as compared to a conventional solid dilator tip. In some embodiments, the surface area of the dilator tip 100 that engages tissue may be 40% to 50% less than the surface area of a conventional solid dilator tip.

The dilator tip 100 may include a proximal plate 106 and the ribs 102 may extend between the distal tip region 104 the proximal plate 106, as shown in FIG. 1. The proximal plate 106 may provide an attachment structure for attaching a separately produced dilator tip 100 to a dilator shaft (not shown). In other embodiments, the distal tip region 104 and proximal plate 106 may be absent, and the ribs 102 may extend between and define the distal end 110 and the proximal end 120 of the dilator tip 100.

Figure 2:
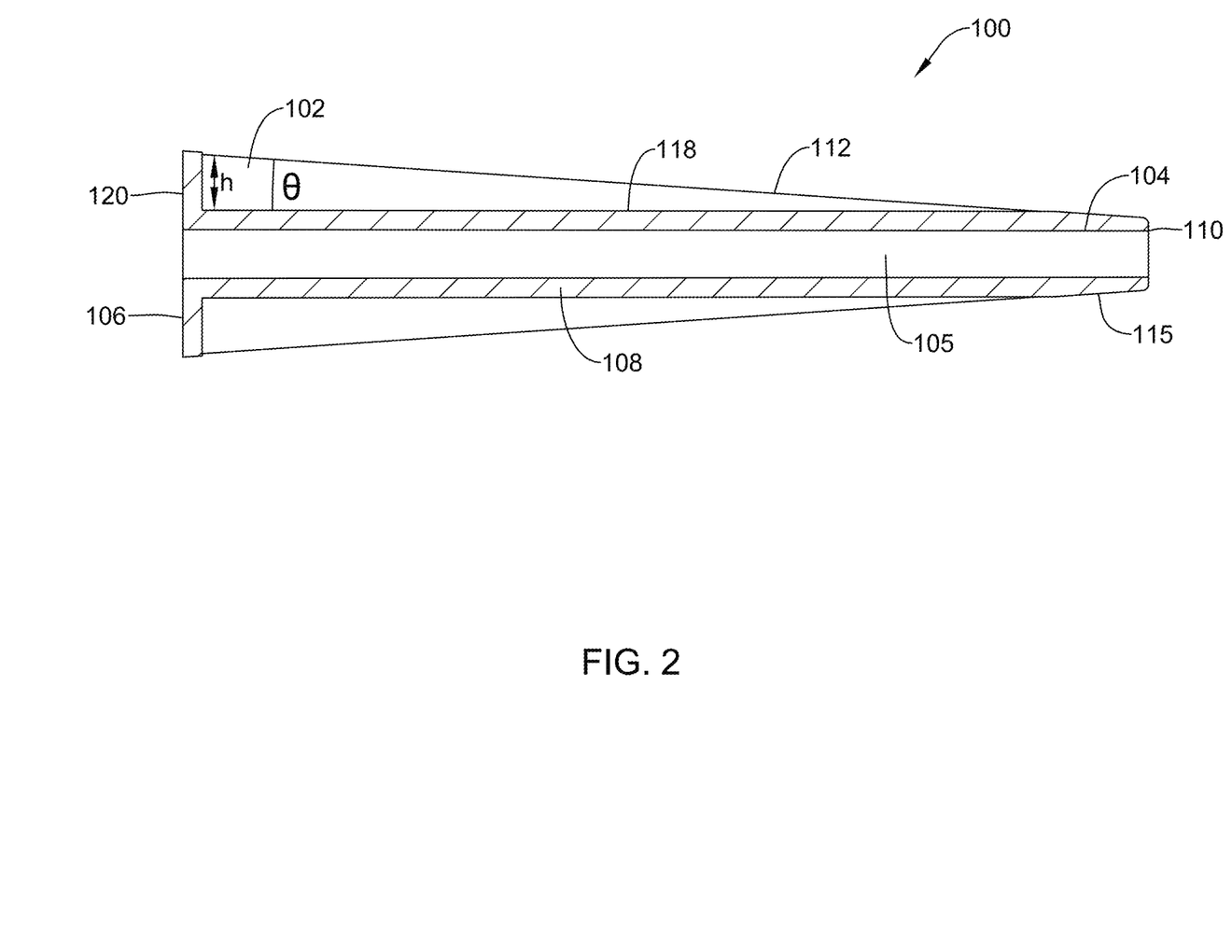
FIG. 2 is a side cross-sectional view of the dilator tip of FIG. 1, taken along line 2-2 in FIG. 1.

As shown in FIG. 2, the ribs 102 may have a base 118 and a top surface 112. The base 118 may be attached to an elongated tubular member 108 that extends between and connects the distal tip region 104 and the proximal plate 106. The tubular member 108 may define a lumen 105 extending longitudinally along the length of the dilator tip 100. The proximal plate 106 may be a solid disc with a central opening defining a portion of the lumen 105. The lumen 105 may allow the dilator tip 100 to be moved over a guide wire. In some embodiments the circumferential wall 115 of the distal tip region 104 may be defined by a distal end of the tubular member 108. The wall thickness of the tubular member 108 may be tapered in the distal tip region 104 such that the distal end 110 is thinner than the remainder of the tubular member 108, as shown in FIG. 2. The overall shape of the dilator tip 100 may be frustoconical, with a conical distal tip region 104 and the ribs 102 having a height extending radially outward from the base 118 to the top surface 112, where the height gradually increases from the distal tip region 104 to the proximal plate 106. The ribs 102 may generally be rigid to provide the dilation desired. However, in some embodiments, the ribs 102 may have a slight flexibility. In still other embodiments, the ribs 102 may have a variable stiffness, with a distal portion of the ribs 102 adjacent the distal tip region 104 having a first stiffness and a proximal portion of the ribs 102 adjacent the proximal plate 106 having a second stiffness, where the second stiffness is greater than the first stiffness. In some embodiments, the stiffness of the ribs 102 may increase gradually from the distal end region 104 to the proximal plate 106.

In some embodiments, the top surface 112 of each of the plurality of ribs 102 may extend from an outer surface of the distal tip region 104 to an outer surface of the proximal plate 106. As shown in FIG. 2, the overall shape of the ribs 102 when viewed from the side may be triangular. Each of the ribs 102 may have a flat top surface 112. In other embodiments, the ribs 102 may have a slightly curved convex, slightly curved concave, or outwardly pointed top surface 112. The ribs 102 may all have the same height profile. The height profile of each rib 102 may be defined as a combination of the height h of the rib 102 at the proximal plate 106, the height at the distal tip region 104, and an angle Θ measured between the base 118 and the top surface 112. In some examples, the angle Θ may be less than 45 degrees or less than 20 degrees. In other examples, the angle Θ may be between 1 degree and 20 degrees or between 2 degrees and 10 degrees, which may provide a reduced friction force when passing through tissues.

Figure 3:
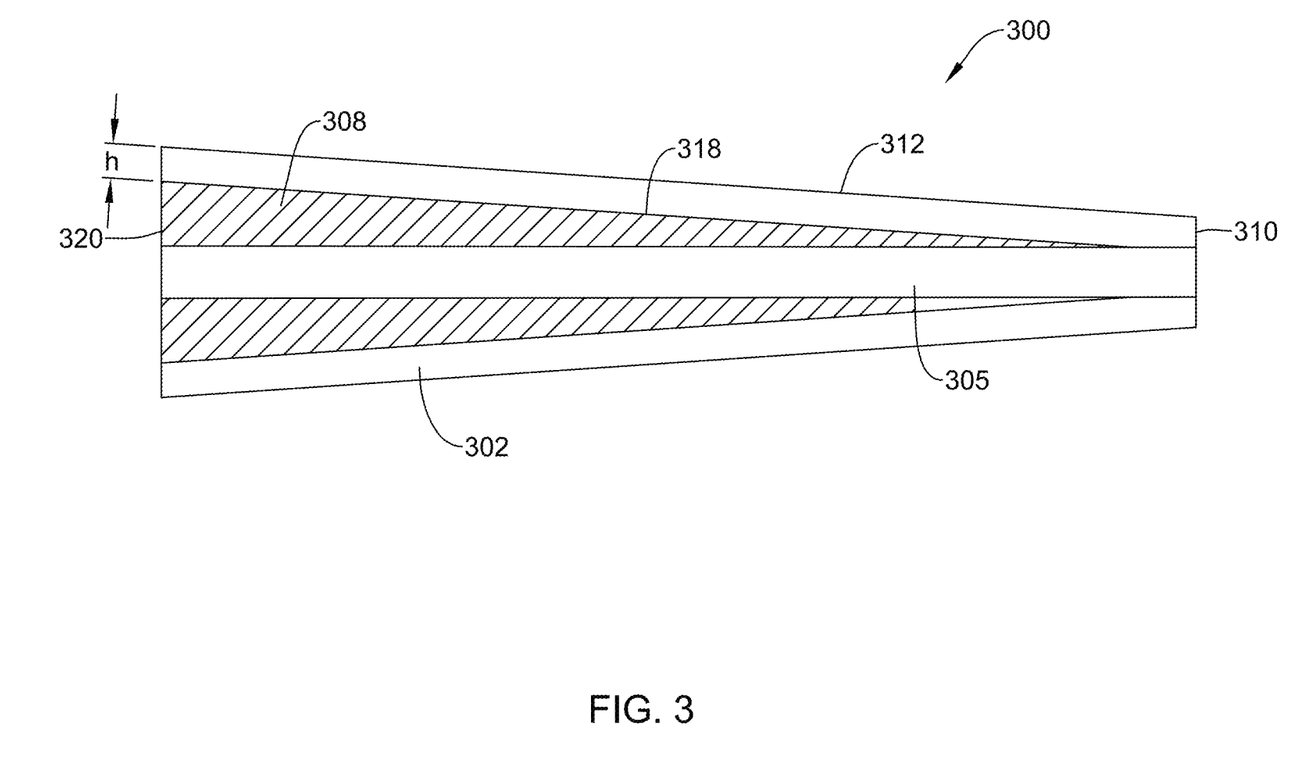
FIG. 3 is a side cross-sectional view of another example dilator tip.

In some embodiments, as shown in FIG. 2, the tubular member 108 may be cylindrical with a substantially constant thickness along its length extending between the distal tip region 104 and the proximal plate 106. In other embodiments, as shown in FIG. 3, the tubular member 308 of the dilator tip 300 may be conical with a thickness that increases from the distal end 310 to the proximal end 320, and be devoid of a circumferential distal tip region and proximal plate. The tubular member 308 may define a lumen 305 extending longitudinally along the length of the dilator tip 300. The ribs 302 may extend between and define the distal end 310 and the proximal end 320 of the dilator tip 300. The ribs 302 may have a base 318 attached to the tubular member 308 and a free top surface 312. The ribs 302 may have a height h extending radially outward from the base 318 to the top surface 312. The height h may be substantially the same along the length of the ribs 302, as shown in FIG. 3. In other embodiments, the height may gradually increase from the distal end 310 to the proximal end 320 of the ribs 302, similar to the ribs 102 shown in FIG. 2. The rigidity/flexibility of the ribs 302, the shape of the top surface 312, and the height profile of each rib 302 may be as discussed above with regard to the ribs 102.

Figure 4:
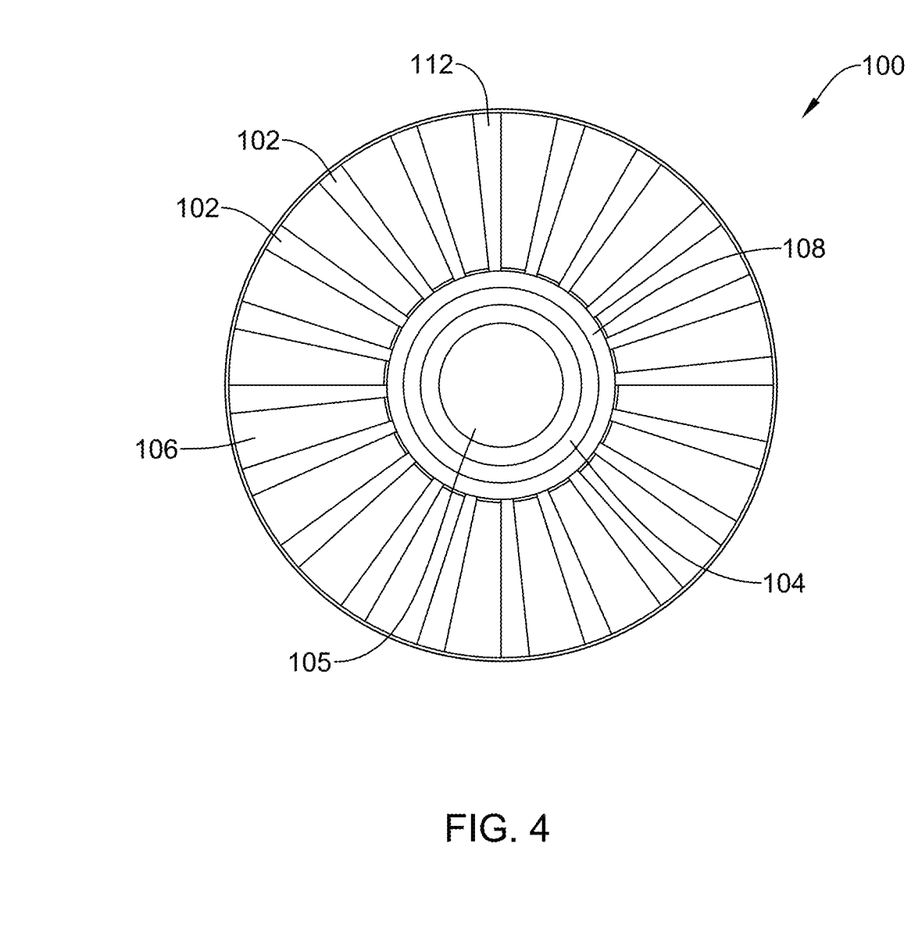
FIG. 4 is a front view of the dilator tip of FIG. 1.

In some embodiments, the overall cross-sectional shape of the dilator tip 100 may be circular, as shown in FIG. 4.

The ribs 102 may extend substantially perpendicular from the tubular member 108, giving the dilator tip 100 its circular cross section. As seen in FIG. 4, the lumen 105 extends through the entirety of the dilator tip 100, from the distal tip region 104 to the proximal plate 106. The top surface 112 of the ribs 102 may extend seamlessly from the outer surface of the distal tip region 104 to the outer surface of the proximal plate 106.

Figure 5:
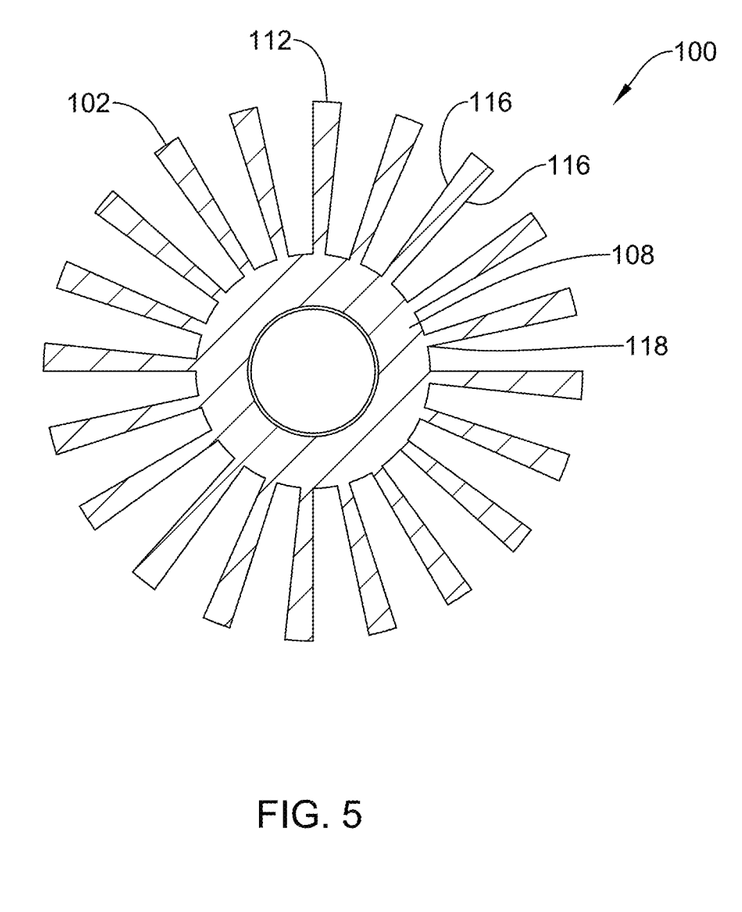
FIG. 5 is a rear cross-sectional view of the dilator tip of FIG. 1, taken along line 5-5 in FIG. 1.

In some embodiments, the ribs 102 may have a first width at the base 118 and a second width at the top surface 112, with the second width being greater than the first width, as shown in FIG. 5. The side walls 116 may extend from the tubular member 108 at a 90 degree angle. With a circular tubular member 108, this results in the second width at the top surface 112 being larger than the first width at the base 118. In other embodiments, the side walls 116 may extend from the tubular member 108 at an angle greater than or less than 90 degrees, creating ribs 102 having rectangular or more tapered cross sections. As shown in FIGS. 4 and 5, the ribs 102 may all have the same height, resulting in an overall circular cross section. In other embodiments, the height of the ribs 102 may vary around the circumference of the dilator tip 100, giving the dilator tip 100 an oval, egg shaped, or undulating cross sectional shape (not shown).

The number of ribs 102, their thickness, and geometry of the top surface 112 (flat, convex, concave, or pointed) may vary depending on the flexibility of the material forming the dilator tip 100 and/or on the stiffness of the tissue wall to be traversed. Additionally the shape and/or material forming the distal tip region 104 may be chosen to achieve a desired flexibility. In some embodiments, the width of the ribs 102 at the base 118 may increase gradually towards the proximal plate 106 (not shown). In some embodiments, the dilator tip 100 may include at least 4 ribs 102. In other embodiments, the dilator tip 100 may include at least 10 ribs 102. In some embodiments, the dilator tip 100 may include between 4-50 ribs 102. In other embodiments, the dilator tip 100 may include between 8-30 ribs 102. As shown in FIG. 5, the dilator tip 100 includes 20 ribs 102.

Figure 6:
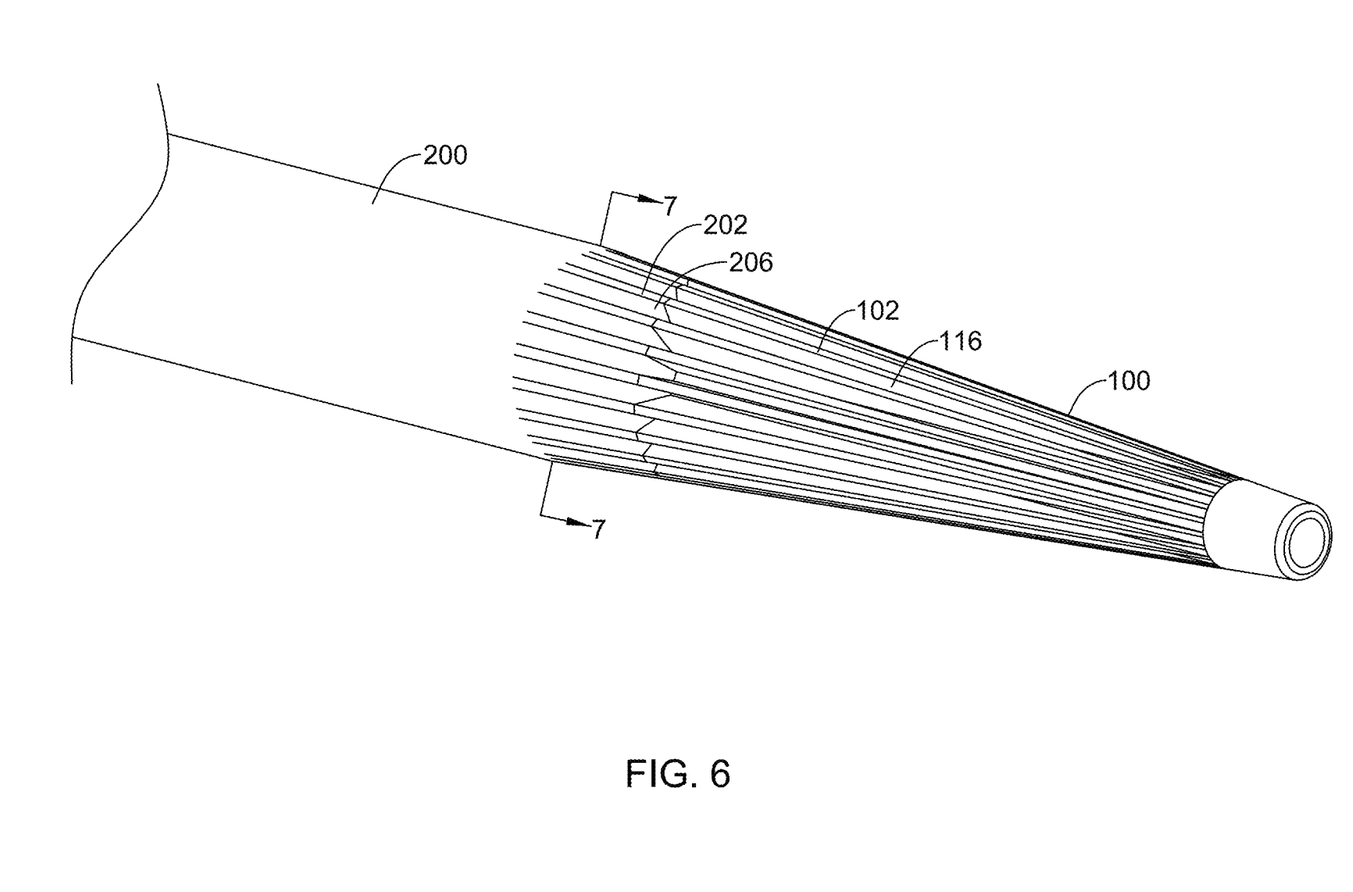
FIG. 6 is a perspective view of the dilator tip of FIG. 1 coupled with a sheath.
Figure 7:
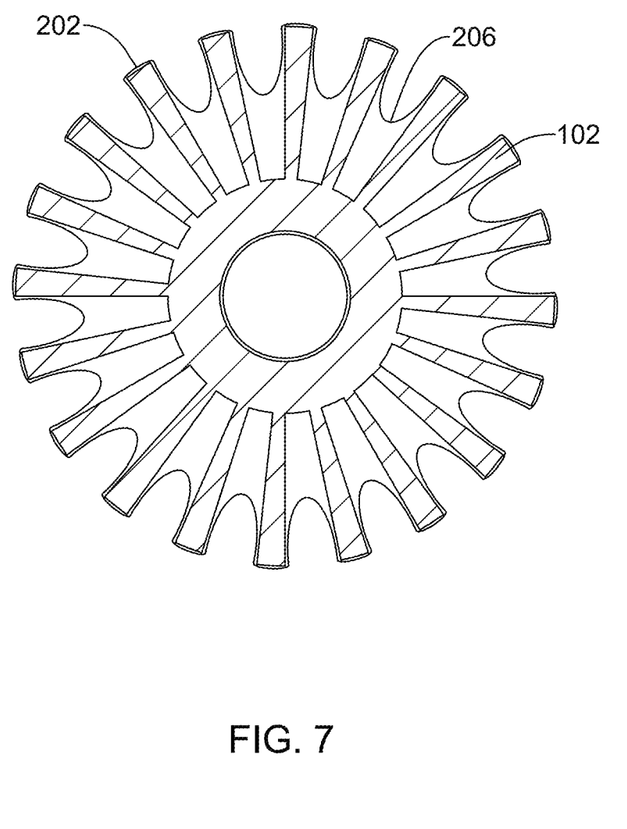
FIG. 7 is a front cross-sectional view of the dilator tip of FIG. 6.

FIG. 6 illustrates an example dilator tip 100 attached to a dilator sheath 200. The distal end of the sheath 200 may conform to the ribs 102, thereby reducing the overall surface area of the dilator top 100 to sheath 200 transition, which may also reduce the friction force when the dilator tip 100 and sheath 200 are moved through a tissue wall. The sheath 200 may be disposed over only a proximal region of the ribs 102, as shown in FIG. 6. In other embodiments, the sheath 200 may be disposed over the entire dilator tip 100 (not shown). The sheath 200 may include a plurality of pleats at the distal end, the pleats defined by alternating peaks 202 and valleys 206, with the peaks 202 sized to fit over and engage the ribs 102 and the valleys 206 sized to be disposed within the spaces between the ribs 102. The valleys 206 may engage at least a portion of the side walls 116 of the dilator tip 100. As seen in the cross section of FIG. 7, the valleys 206 of the sheath may extend only partially into the space between the ribs 102, while the peaks 202 are in direct contact with the ribs 102. In some embodiments, the sheath 200 may follow all contours of the dilator tip 100, such that no space is present between the outer surface of the dilator tip 100 and the sheath 200. The sheath 200 may be bonded to the dilator tip 100 using heat, adhesive, over-molding, or other conventional method of attaching a distal tip to a sheath. In some embodiments, the peaks 202 and valleys 206 at the distal end of the sheath 200 may be formed as the sheath 200 is placed over the ribs 102 of the dilator tip 100 and attached thereto. For example, the distal end of the sheath 200 may be placed over the dilator tip 100 and then molded into the peaks 202 and valleys 206. In other embodiments, the peaks 202 and valleys 206 may be formed at the distal end of the sheath 200 prior to attaching the sheath 200 to the dilator tip 100. For example, the sheath 200 may be pleated to form the peaks 202 and valleys 206. In another example, at least the region of the sheath 200 forming the peaks 202 and valleys 206 may be made of a shape memory polymer. The sheath 200 may have a substantially cylindrical configuration under a first set of conditions, and may transition to the peaks 202 and valleys 206 under a second set of conditions. The first and second set of conditions may include the application of heat, cold, an electrical current, or any other conditions necessary for transitioning a shape memory polymer.

Figure 8:
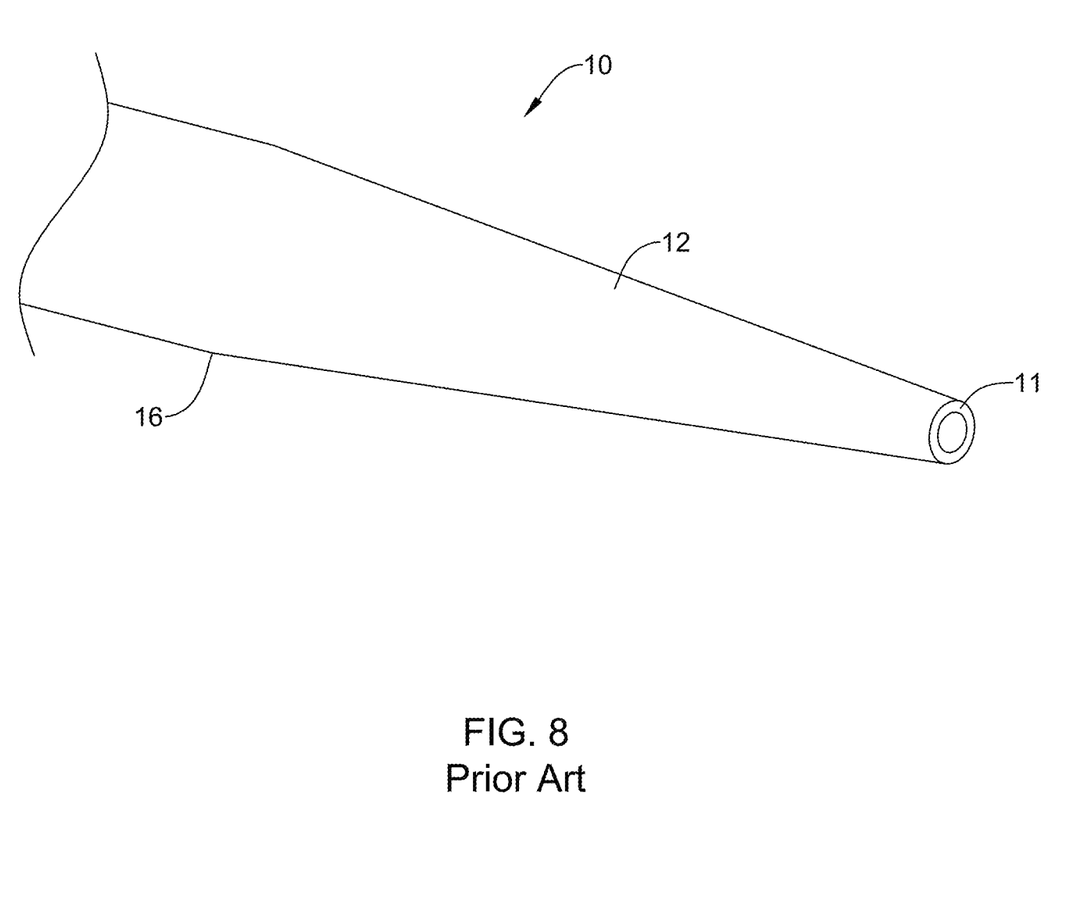
FIG. 8 is a perspective view of a conventional solid dilator tip.
Figure 9:
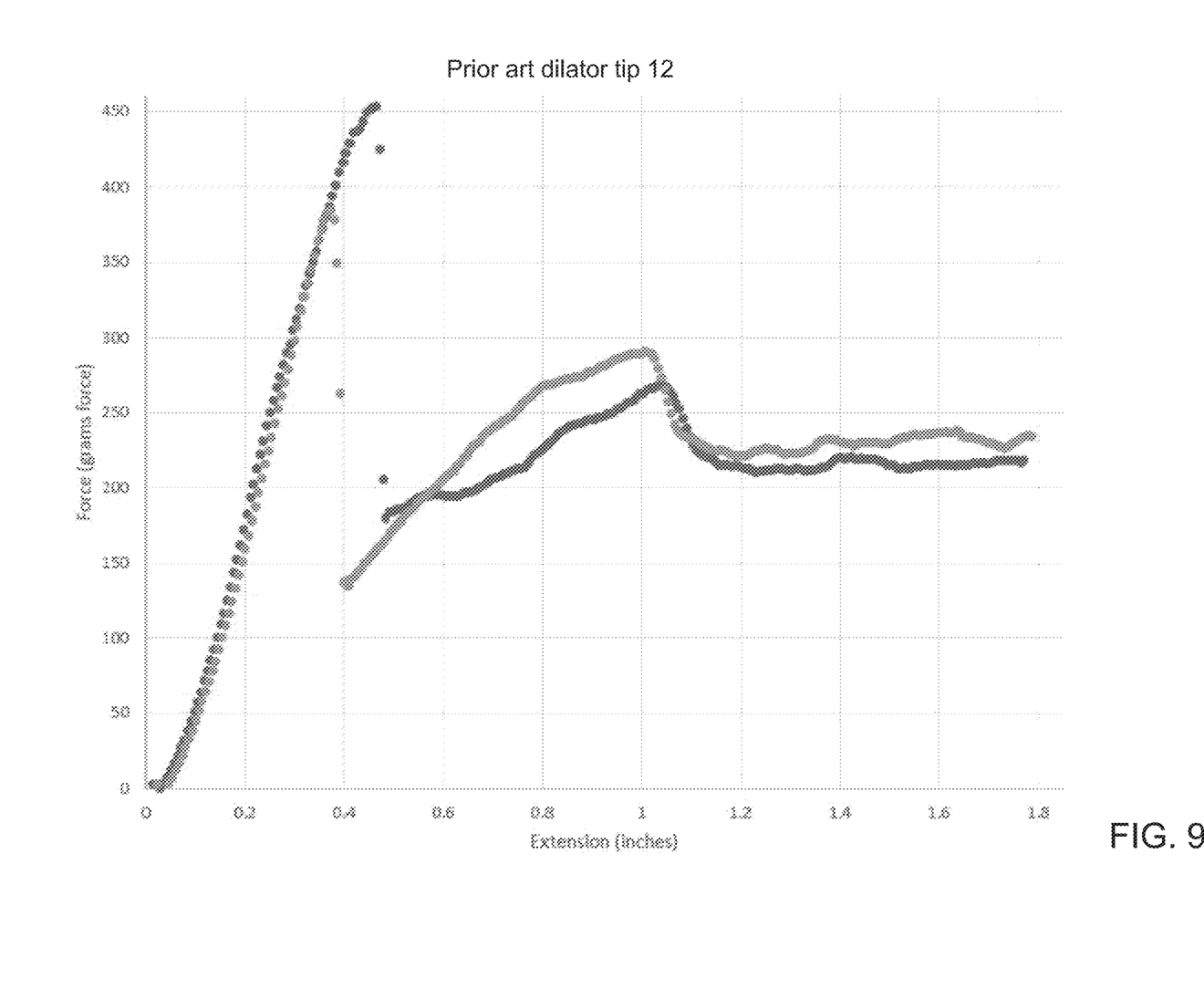
FIG. 9 is a graph showing the force profile along a conventional solid dilator tip.

Conventional dilator-sheath assemblies 10 generally have a solid, circumferentially continuous walled dilator tip 12, as shown in FIG. 8. These dilator tips 12 have pronounced force peaks at points when the dilator tip and dilator-sheath assemblies are entered into the skin, or cross tissue walls inside of the body. These force peaks occur in relation to the location of the dilator tip, when the distal tip 11 of the dilator crosses the tissue barrier, and at the transition 16 to the maximum outer diameter of the sheath. FIG. 9 illustrates the forces acting on a conventional solid, circumferentially continuous walled dilator tip, as shown in FIG. 8, as the dilator tip crosses a sample of 40A hardness silicone rubber. The two series of dots represent two different measurements of force on the same tip. In FIG. 9, the initial force peak of 400-450 grams of force occurs around 0.4 inches, when the distal tip 11 passes through the silicone rubber material. The force drops off to 140 to 180 grams force and then increases steadily between 0.4 inches and 1 inch as the diameter of the dilator tip increases, up to another force peak of 260-290 grams force around 1 inch, as the transition 16 to the maximum outer diameter of the dilator tip is moved through the silicone rubber material.

Figure 10:
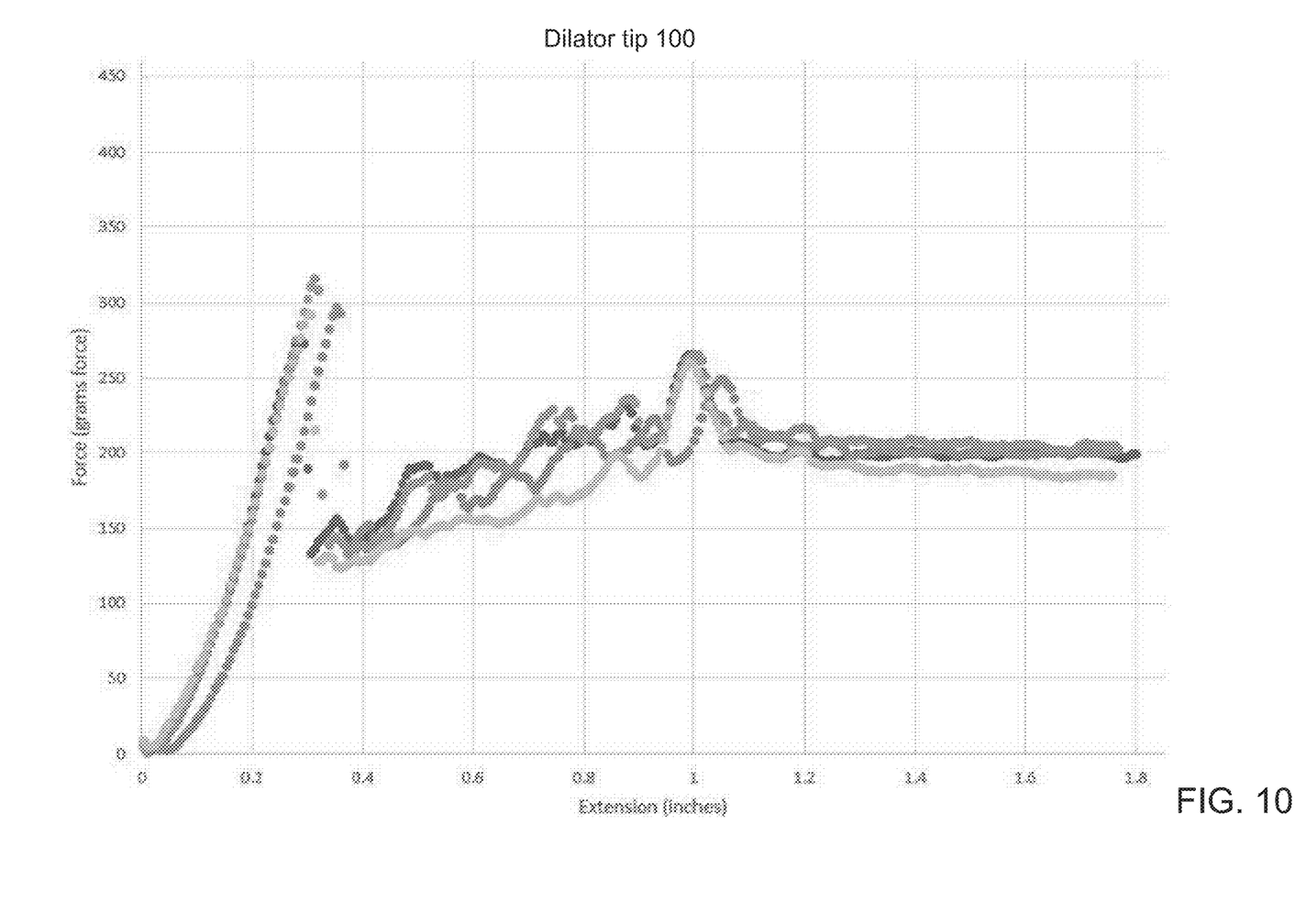
FIG. 10 is a graph showing the force profile along the dilator tip of FIG. 1.

FIG. 10 illustrates the forces acting on an example dilator tip 100, as show in FIG. 1, as the dilator tip 100 crosses the same sample of 40A hardness silicone rubber. The four series of dots represent four different measurements of force on the same tip.

In FIG. 10, the initial force peak of 275-310 grams of force occurs around 0.3 inches, when the distal end 110 passes through the silicone rubber material. The force drops off to 125 to 150 grams force and then increases between 0.3 inches and 1 inch as the diameter of the dilator tip increases, up to another force peak of 250-260 grams force around 1 inch, as the proximal plate 106 transitions to the maximum outer diameter of the dilator tip.

As seen in the differences between FIGS. 9 and 10, the dilator tip 100 with ribs 102 reduces the force peaks at the initial distal tip and at the transition to maximum outer diameter. Additionally, the angle of the force increase between the distal end passing through and the maximum outer diameter passing through the material is significantly reduced, indicating a more gradual increase in force as well as the overall reduction in total force created as the dilator tip 100 moves through the silicon rubber material. This reduction in force provides the advantage of the operator needing less force to move the dilator tip and associated sheath into the body and across various tissue walls, which may reduce tissue damage.

The materials that can be used for the various components of the dilator tip 100 disclosed herein may include those commonly associated with medical devices. For simplicity purposes, the following discussion makes reference to the dilator tip 100 (and variations, systems or components disclosed herein). However, this is not intended to limit the devices and methods described herein, as the discussion may be applied to other elements, members, components, or devices disclosed herein.

In some examples, the dilator tip 100 may be made of polymer. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In other examples, the plurality of ribs 102 may be made of a shape memory material, such as a shape memory polymer. The shape memory ribs 102 may be attached to a solid walled tubular member 108 made of a different material, or the entire dilator tip 100 may be made of a shape memory material. The entire dilator tip 100, including the distal tip region 104, the ribs 102, proximal plate 106, and tubular member 108 may be formed from a single monolithic piece. In other examples, the ribs 102 and tubular member 108 may be formed from a material different from the distal tip region 104 and proximal plate 106, with the three regions attached during manufacture. The ribs 102 may be formed by molding, using any molding technique, or by removing/ablating material from a solid mass. In some embodiments, the dilator tip 100 may be formed with a dilator sheath (not shown) as a single monolithic structure.

In at least some embodiments, portions or all of the dilator tip 100 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the dilator tip 100 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the dilator tip 100 (and variations, systems or components thereof disclosed herein) to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A dilator tip comprising:
   an elongated tubular member defined by a circumferential wall and having a distal tip region and a proximal end; and
   a plurality of ribs, every rib extending longitudinally between the distal tip region and the proximal end of the elongated tubular member, the plurality of ribs extending radially outward from the elongated tubular member, the plurality of ribs spaced apart circumferentially, wherein at the proximal end of the elongated tubular member, each of the plurality of ribs has a first radial height greater than a width, wherein a radially outward facing top surface of each of the plurality of ribs extends from the proximal end at a continuous uniform angle to the distal tip region.

2. The dilator tip of claim 1, wherein the elongated tubular member and the plurality of ribs are all formed from a single monolithic piece.

3. The dilator tip of claim 1, wherein the elongated tubular member and the plurality of ribs are formed from a polymer.

4. The dilator tip of claim 1, wherein each of the plurality of ribs has a second radial height at the distal tip region of the elongated tubular member, wherein the second radial height is smaller than the first radial height.

5. The dilator tip of claim 4, wherein the radially outward facing top surface of each of the plurality of ribs extends between the distal tip region and the proximal end at an angle of between 1 degree and 20 degrees.

6. The dilator tip of claim 1, further comprising a proximal plate extending radially outward from the proximal end of the elongated tubular member, wherein the plurality of ribs extend between the distal tip region and the proximal plate.

7. The dilator tip of claim 1, wherein the width of each of the plurality of ribs includes a first width at a base adjacent the elongated tubular member, and a second width at a top surface of each of the plurality of ribs, wherein the second width is larger than the first width and the first and second widths are measured at a single longitudinal location.

8. The dilator tip of claim 1, wherein the top surface of each of the plurality of ribs is flat.

9. The dilator tip of claim 1, wherein the plurality of ribs includes 4-50 ribs.

10. The dilator tip of claim 9, wherein the plurality of ribs includes 20 ribs.

11. The dilator tip of claim 1, further comprising a sheath attached to a proximal end of the plurality of ribs, the sheath extending proximally from the dilator tip.

12. The dilator tip of claim 11, wherein a distal end of the sheath includes a plurality of pleats configured to conform to the plurality of ribs and spaces between the plurality of ribs.

13. The dilator tip of claim 12, wherein the plurality of pleats includes alternating peaks and valleys, wherein the peaks are configured to engage the plurality of ribs and the valleys are configured to be disposed within the spaces between the plurality of ribs.

14. The dilator tip of claim 13, wherein the valleys are configured to extend only partially into the spaces between the plurality of ribs.

15. The dilator tip of claim 11, wherein a distal end of the sheath is positioned distal of the proximal end of the plurality of ribs such that a distal region of the sheath is disposed over only a proximal region of the plurality of ribs.

16. The dilator tip of claim 1, wherein the distal tip region is defined by a circumferential wall joining the radially outward facing top surface of each of the plurality of ribs.

17. A dilator tip comprising:
an elongated tubular member defined by a circumferential wall and having a distal tip region; and
a plurality of ribs extending longitudinally and proximally from the distal tip region, the plurality of ribs extending radially outward from the elongated tubular member, the plurality of ribs spaced apart circumferentially, wherein the plurality of ribs have a first height at the distal tip region and a second height at a proximal end thereof, wherein the second height is larger than the first height, wherein each of the plurality of ribs has a variable stiffness, with a distal portion of each rib adjacent the distal tip region having a first stiffness and a proximal portion of each rib adjacent the proximal end having a second stiffness, wherein the second stiffness is greater than the first stiffness.

18. The dilator tip of claim 17, wherein each of the plurality of ribs has a first width at a base adjacent the elongated tubular member, and a second width at a top surface of each of the plurality of ribs, wherein the second width is larger than the first width and the first and second widths are measured at a single longitudinal location.

19. The dilator tip of claim 17, wherein the plurality of ribs includes 4-50 ribs.

20. A dilator tip comprising:
an elongated tubular member defined by a circumferential wall and having a distal tip region;
a plurality of ribs extending longitudinally and proximally from the distal tip region, the plurality of ribs extending radially outward from the elongated tubular member, the plurality of ribs spaced apart circumferentially, wherein the plurality of ribs have a first height at the distal tip region and a second height at a proximal end thereof, wherein the second height is larger than the first height; and
a sheath attached to the proximal end of the plurality of ribs, the sheath including a plurality of pleats configured to conform to the plurality of ribs and spaces between the plurality of ribs, the plurality of pleats including alternating peaks and valleys, wherein the peaks are configured to engage the plurality of ribs and the valleys are configured to be disposed within the spaces between the plurality of ribs.

* * * * *